United States Patent [19]

Shaw et al.

[11] Patent Number: 4,958,042

[45] Date of Patent: Sep. 18, 1990

[54] DIMERIZATION OF ACRYLONITRILE

[75] Inventors: Gordon Shaw, Guisborough; Jose Lopez-Merono, Marske, both of England

[73] Assignee: Imperial Chemical Industries PLC, London, England

[21] Appl. No.: 262,582

[22] Filed: Oct. 26, 1988

[30] Foreign Application Priority Data

Oct. 28, 1987 [GB] United Kingdom ............... 8725218

[51] Int. Cl.$^5$ .................. C07C 253/30; C07C 255/04
[52] U.S. Cl. .................................................. 588/363
[58] Field of Search ........................................ 558/363

[56] References Cited

U.S. PATENT DOCUMENTS 4,102,915  7/1978  Jennings et al. ............... 260/465.8
4,316,857  2/1982  Gilbert ............................... 558/363
4,639,539  1/1987  Hovey et al. ..................... 558/363

FOREIGN PATENT DOCUMENTS 2351093  9/1977  France .

*Primary Examiner*—Joseph Paul Brust
*Attorney, Agent, or Firm*—Cushman, Darby & Cushman

[57] ABSTRACT

Acrylonitrile is dimerized in a homogenious liquid phase comprising a phosphinite or phosphonite catalyst, a proton donating solvent and an aromatic and aliphatic hydrocarbon solvent, the aromatic solvent, unconverted acrylonitrile and proton donating solvent is distilled from the product and a mixture is left which separates into two phases, one comprising the catalyst and the other the dinitrile.

11 Claims, No Drawings

DIMERIZATION OF ACRYLONITRILE

This invention relates to the dimerization of acrylonitrile.

It is known to dimerize acrylonitrile to a linear $C_6$ dinitrile in a liquid phase comprising a phosphonite or phosphinite catalyst and an inert proton donating solvent.

In U.S. Pat. No. 4,316,857 such a process is disclosed in which an aliphatic hydrocarbon (co-) solvent preferably boiling in the range 30° to 150° C. and an aromatic hydrocarbon (co-) solvent preferably boiling in the range 75° to 150° C. are present and in which the product is cooled to form two phases, one phase comprising catalyst and the other the dinitrile. The (co-) solvents exemplified are toluene (BP 110.6° C.) together with either methyl cyclohexane (BP 100.3° C.) or petroleum ether (BP 30° -40° C.).

We have found that a process of this type may be improved if the aromatic solvent and inert proton donating solvent are at least partly removed by evaporation or distillation whilst leaving aliphatic solvent in that the separation of catalyst from product is better. Also once the proton donating solvent and unconverted acrylonitrile are removed with the aromatic solvent less unwanted side reaction occurs. Both the inert proton donating solvent and the aromatic solvent are preferably substantially lower in boiling point than the aliphatic solvent and product. Improved separation of product from the catalyst also minimizes further reactions which consume the product, and because phase separation will generally occur in distillation columns further reaction during the distillation stage itself is readily kept at modest levels. If distillation is at a temperature below 100° C. and more preferably below 85° C. the residence time during distillation is preferably at most fifteen minutes and more preferably at most five or ten minutes.

This invention therefore comprises a process which comprises dimerizing acrylonitrile to a linear $C_6$ dinitrile in a homogeneous liquid phase which comprises a phosphinite or phosphonite catalyst and an inert proton donating solvent, an aromatic hydrocarbon solvent and an aliphatic or cycloaliphatic hydrocarbon solvent characterized in that the aliphatic or cycloaliphatic solvent boils at a temperature higher than the aromatic solvent, inert proton donating solvent, and acrylonitrile and in which the aromatic solvent, unconverted acrylonitrile and inert proton donating solvent is evaporated or distilled from the reaction product preferably at a temperature of 50° to 100° C. to leave a mixture which separates into two phases, one of which comprises a major proportion of the catalyst and the other comprises a major proportion of the linear $C_6$ dinitrile.

Suitable phosphinites and phosphonites are of general formula:

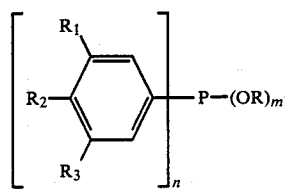

which $R_1$, $R_2$ and $R_3$ are individually hydrogen atoms or electron donating substituents which are free from active hydrogen atoms.

Suitable electron donating substituents are alkyl or alkoxy groups having for example 1 to 12 and preferably 1 to 3 carbon atoms, or $R_4R_5N$- groups having 1 to 10 and preferably 1 to 6 carbon atoms in the form of two alkyl substituents $R_4$ and $R_5$. Preferably at least the group $R_2$ is an electron donating substituent. Either $R_1$ or $R_3$ may form part of a fused alicyclic ring with $R_2$, R is an alkyl or cycloalkyl group for example having 1 to 12 and preferably 1 to 6 carbon atoms, and n and m are integers, each being either 1 or 2, provided that (m+n) equals 3. When n is 2, the substituents on each aromatic ring may be the same or different and when m is 2 the groups R may be the same or different.

By "electron-donating substituent" we mean a substituent of the aromatic nucleus which gives rise to a negative Hammett $\sigma$ constant.

A discussion on Hammett $\sigma$ constants and a table showing values for most common substituents is to be found in an article by Clark and Perrin in Quarterly Reviews of the Royal Society of Chemistry, vol 18 1964 pp 295-320.

Examples of suitable substituents $R_1$, $R_2$ and $R_3$ include alkoxy groups, e.g. methoxy, ethoxy, i-propoxy and t-butoxy; alkyl groups e.g., methyl, ethyl and propyl; and dialkyl amino groups, e.g. dimethylamino and diethylamino. Groups $R_1$, $R_2$ and $R_3$ which do not contain active hydrogen atoms are those which do not react adversely with the components of the reaction system.

Suitable groups R include alkyl groups such as methyl, ethyl, isopropyl, neopentyl, 2-ethylhexyl; and cycloalkyl groups such as cyclohexyl.

By an "inert" proton donating solvent is meant one which is substantially unreactive with respect to the addition to, or reaction with the unsaturated linkage of the acrylonitrile or the products of the acrylonitrile dimerization. Furthermore, the solvent must not react with the phosphorus compound or catalytic intermediates to form inactive phosphorus species at such a rate as to seriously impair the dimerization reaction.

Preferably hydroxylic solvents, such as alcohols, having 1 to 5 carbon atoms are used. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

The co-solvents tend to reduce the production of polymeric by-products in the reaction, and a high proportion of aromatic solvent reducing blocking of pipelines and the need to filter the reaction product. We prefer that the volume ratio of aromatic solvent to aliphatic and/or cycloaliphatic solvent is in the range 9:1 to 1:1 by volume but preferably in the range 9:1Δ7:3 in order to ensure the dimerization mixture remains in one phase.

Suitable aromatic solvents and inert proton donating solvents are those boiling in the range 80 to 150° C. and preferably 80 to 120° C. and the aliphatic solvents are suitably paraffins or cycloparaffins boiling in the range 150° to 300° C. and preferably 180° to 250° C. Preferably a difference in boiling point of at least 40° C., preferably at least 60° C. and more preferably at least 100° C. should exist between that of the aliphatic solvents on the one hand and the aromatic and inert proton donating solvents on the other. Boiling points and ranges are expressed as at atmospheric pressure.

Suitable aromatic solvents are benzene and mono- or di-alkyl benzenes having at most two carbon atoms in their alkyl group(s) and mixtures thereof. Benzene is preferred because it forms a low boiling azeotrope with acrylonitrile and with isopropanol which can be used as an inert proton donating solvent. Such ready removal of acrylonitrile minimizes by product formation.

Suitable aliphatic solvents have 10 to 16 and preferably 12 to 14 carbon atoms, for example decalin and linear or branched alkanes and cycloalkanes.

The reaction must be conducted in the substantial absence of water. We believe that the water reacts with the catalyst in the presence of acrylonitrile to deactivate the catalyst. Thus, the acrylonitrile, proton-donating solvent and co-solvents must be dried before use, otherwise the reaction may be inhibited. In particular acrylonitrile, which commonly contains as much as 4000 ppm of water, even after distillation, must be rigorously dried. Acrylonitrile stabilizers of the phenolic type, for example hydroquinone stabilizers, if present in acrylonitrile as supplied, should be removed if catalyst deactivation is to be avoided.

Any suitable drying technique may be used provided that the final water level is sufficiently low. For example, acrylonitrile and hydroxylic solvents may be dried by being contacted with calcium hydride or a 3A or 4A molecular sieve.

The concentration of the phosphorus compound in the reactant mixture may be varied over a wide range, for example, from 0.001, commonly 0.1, to 20% by volume, calculated on the volume of liquid reactants, but preferably the concentration is in the range 0.01 to 10% by volume.

The reaction temperature is commonly in the range 0° to 120° C., but it is generally preferred to keep the temperature below 75° C. to minimize polymerization of the acrylonitrile and dimeric products. Preferably, the reaction temperature is in the range 20° to 70° C.

In a continuous reaction the proportion of acrylonitrile in the total feed is preferably in the range 5 to 25% and preferably 10 to 15% by weight. The combined concentrations of aromatic and aliphatic solvents in the reaction medium is suitably 60 to 90% and preferably 65 to 80% by weight.

Pressures in the process are suitably those arising from the materials present at the relevant temperatures.

The phase comprising a major proportion of the catalyst may be recycled to the reaction, as may evaporated or distilled aromatic solvent and inert proton donating solvent and acrylonitrile, with appropriate make-up with fresh materials. The phase containing a major proportion of the linear $C_6$ dinitrile product may be washed with hydrocarbons to remove any remaining catalyst and solvents before being processed, for example in known manner, to recover the linear $C_6$ dinitrile.

EXAMPLE 1

A feed of composition 5.6% isopropanol, 11.6% acrylonitrile, 61.6% benzene, 13.6% aliphatic hydrocarbon solvent consisting essentially of branched chain $C_{12}$ alkanes (EC180) and 5.4% isopropyl bis-p-tolyl phosphinite catalyst (all percentages being by weight) was passed into a continuous plug flow reactor held at a reaction temperature of 60° C. and with a residence time of 6.5 hours. The effluent from the reactor was fed at a rate of 60 ml/hour to the top of a sealed jacketed glass column 55 cm long and 3 cm internal diameter packed with 3 mm diameter glass beads. The base of the packed column was attached to a falling film reboiler with a wall temperature of 55° C. provided by a hot water supply to the outer jacket. The distillation action in the column was provided by a single pass of dry deoxygenated nitrogen at a rate of 45 l/hour entering just below the reboiler. The exit stream from the reboiler was cooled before entering a phase separator from which hydrocarbon top phase and the dicyanobutene rich lower phase passed into their respective storage vessels. The overhead stream from the distillation column was condensed and collected for recycle to the reactor. The results shown in the Table 1 were obtained on two occasions over a two day period.

TABLE

| | | STREAM COMPOSITION % w/w | | | | | | | | |
|---|---|---|---|---|---|---|---|---|---|---|
| Stream | Test | Isopropanol | Acrylonitrile | Benzene | EC180 | MEGN Trimers | DCB | AN | Catalyst | Total |
| Reactor Effluent Feed to Distillation Column (RE) | 1 | 5.7 | 2.1 | 61.9 | 13.6 | 0.5 | 8.9 | 0.4 | 5.1 | 98.2 |
| | 2 | 5.8 | 2.0 | 61.7 | 13.9 | 0.6 | 9.1 | 0.4 | 5.4 | 98.0 |
| Phase Separator Upper Layer (UL) | 1 | 0 | 0 | 17.3 | 60.6 | 0.1 | 1.0 | 0.1 | 20.0 | 99.1 |
| | 2 | 0 | 0 | 17.7 | 61.5 | 0 | 1.0 | 0.1 | 20.4 | 100 |
| Phase Separator Lower Layer (LL) | 1 | 0 | 0 | 20.8 | 2.0 | 3.6 | 61.9 | 3.7 | 7.3 | 99.3 |
| | 2 | 0 | 0 | 17.3 | 1.5 | 3.8 | 64.8 | 4.0 | 7.9 | 99.3 |

MEGN means methylene glutaronitrile
DCB means dicyanobutene (mixture of cis and trans dicyanobutene-1 and dicyanobutene-2)
AN means acrylonitrile. EC 180 is the aliphatic hydrocarbon solvent The results shown in Table 2 illustrate the extent to which the catalyst and dicyanobutene product pertitioned at the phase separation stage based on the analysis of the analysis data.

TABLE 2

| Test | % of Catalyst Recovered in Upper Layer | % of Dicyanobutene Recovered in Lower Layer |
|---|---|---|
| 1 | 81.0 | 97.9 |

TABLE 2-continued

| Test | % of Catalyst Recovered in Upper Layer | % of Dicyanobutene Recovered in Lower Layer |
|---|---|---|
| 2 | 80.6 | 97.6 |

EXAMPLE 2

Example 1 was repeated with a reactor feed of composition 5.5% isopropanol, 11.0% acrylonitrile, 23.7% benzene, 38.3% toluene, 12.3% of the aliphatic hydrocarbon solvent EC 180 and 6.3% of the catalyst, by weight. The feed of nitrogen to the distillation stage was at a rate of 80 liters/h.

The results obtained are shown in Table 3.

TABLE 3

| Stream | STREAM COMPOSITION % w/w ||||||||||
|---|---|---|---|---|---|---|---|---|---|---|
| | Isopropanol | Acrylonitrile | Benzene | Toluene | EC180 | MEGN | DIB | TRIMERS | CATALYST | TOTAL |
| Reactor Effluent Feed to Distillation Column (RE) | 5.1 | 1.2 | 24.1 | 39.0 | 12.6 | 0.4 | 8.0 | 0.4 | 6.3 | 97.1 |
| Phase Separator Upper Layer (UL) | 0 | 0 | 0 | 2.4 | 62.9 | 0 | 0.5 | 1.1 | 30.9 | 97.8 |
| Phase Separator Lower Layer (LL) | 0 | 0 | 0 | 2.2 | 0.7 | 3.9 | 75.8 | 4.0 | 10.6 | 97.2 |

Further calculations based on the results in Table 3 give the catalyst and dicyanobutene product partition results at the phase separation stage shown in Table 4.

TABLE 4

| Example No. | % if Catalyst Recovered in Upper Layer | % of Dicyanobutene Recovered in Lower Layer |
|---|---|---|
| 2 | 85.6 | 97.0 |

The above data show that this mode of operation does not lead to any significant oligomerization or polymerization of the dicyanobutene product by the catalyst system.

All analytical data are by gas/liquid chromatography.

We claim:

1. In a process which comprises dimerizing acrylonitrile to a linear $C_6$ dinitrile in a homogeneous liquid phase which comprises a phosphinite or phosphonite catalyst and an inert proton donating solvent, an aromatic hydrocarbon solvent and an aliphatic or cycloaliphatic hydrocarbon solvent, the improvement wherein the aliphatic or cycloaliphatic solvent is one which boils at a temperature higher than the aromatic solvent, inert proton donating solvent, and acrylonitrile, the boiling point of the aliphatic or cycloaliphatic hydrocarbon solvent being at least 40° higher than that of the aromatic solvent and inert proton donating solvent, and the aromatic solvent, unconverted acrylonitrile and inert proton donating solvent are evaporated or distilled from the reaction product to leave a mixture which separates into two phases, one of which comprises a major proportion of the catalyst and the other of which comprises a major proportion of the linear $C_6$ dinitrile.

2. A process as claimed in claim 1 in which the proton donating solvent comprises a secondary or tertiary alcohol.

3. A process as claimed in claim 2 in which the molar concentration of the proton donating solvent is greater than that of phosphonite or phosphonite catalyst.

4. A process as claimed in claim 1 in which the combined concentrations of aromatic and aliphatic and/or cycloaliphatic solvents in the reaction medium is 60 to 90% and the volume ratio of aromatic to aliphatic solvents is in the range 9:1 to 7:3.

5. A process as claimed in claim 1 in which the inert proton donating solvent and aromatic solvent boil in the range 80° to 150° C., the aliphatic solvent boils in the range 150° to 300° C. and a difference in boiling points of at least 40° C. exists between the boiling point of the aliphatic solvent on the one hand and the inert proton donating solvent and the aromatic solvent on the other.

6. A process as claimed in claim 1 in which the aromatic solvent is benzene and the proton donating solvent is isopropanol.

7. A process as claimed in claim 1 in which the concentration of the phosphorus compound is 0.01 to 10% by volume.

8. A process as claimed in claim 1 in which the reaction temperature is 20° to 70° C.

9. A process as claimed in claim 1 in which evaporated or distilled aromatic solvent, proton donating solvent, acrylonitrile and the phase comprising a major proportion of the catalyst is recycled to the reaction.

10. A process as claimed in claim 1 which a major proportion of the linear $C_6$ dinitrile product is washed with a hydrocarbon to remove any remaining catalyst and solvents before being processed to recover linear $C_6$ nitrile.

11. The process according to claim 4 wherien the phosphinite or phosphonite catalyst is of the general formula:

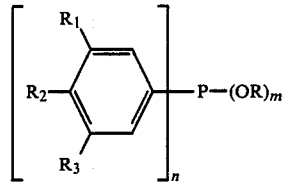

in which $R_1$, $R_2$ and $R_3$ are individually hydrogen atoms or electron donating constituents which are free from active hydrogen atoms, the inert proton donating solvent is a secondary or tertiary alcohol, the aromatic hydrocarbon solvent is benzene, and the aliphatic hydrocarbon solvent is a branched chain $C_{12}$ alkane.

* * * * *